(12) United States Patent
Shchepinov

(10) Patent No.: US 10,029,956 B2
(45) Date of Patent: Jul. 24, 2018

(54) THERAPIES FOR CANCER USING ISOTOPICALLY SUBSTITUTED LYSINE

(75) Inventor: Mikhail S. Shchepinov, Kingston upon Thames (GB)

(73) Assignee: Retrotope, Inc., Los Altos, CA (US)

( * ) Notice: Subject to any disclaimer, the term of this patent is extended or adjusted under 35 U.S.C. 154(b) by 1262 days.

(21) Appl. No.: 12/922,449

(22) PCT Filed: Mar. 13, 2009

(86) PCT No.: PCT/US2009/037161
§ 371 (c)(1),
(2), (4) Date: Dec. 7, 2010

(87) PCT Pub. No.: WO2009/114809
PCT Pub. Date: Sep. 17, 2009

(65) Prior Publication Data
US 2011/0082208 A1    Apr. 7, 2011

Related U.S. Application Data

(60) Provisional application No. 61/036,841, filed on Mar. 14, 2008.

(51) Int. Cl.
*A61K 31/195* (2006.01)
*C07C 229/26* (2006.01)
*C07B 59/00* (2006.01)

(52) U.S. Cl.
CPC .......... *C07B 59/001* (2013.01); *A61K 31/195* (2013.01); *C07C 229/26* (2013.01); *C07B 2200/05* (2013.01)

(58) Field of Classification Search
CPC .................... A61K 31/195; C07C 229/26; C07B 2200/05; C07B 59/001
See application file for complete search history.

(56) References Cited

U.S. PATENT DOCUMENTS

| | | | |
|---|---|---|---|
| 5,846,514 A * | 12/1998 | Foster et al. | 424/1.81 |
| 6,111,066 A | 8/2000 | Anderson et al. | |
| 6,221,335 B1 * | 4/2001 | Foster | 424/1.81 |
| 6,340,578 B1 | 1/2002 | Anderson et al. | |
| 6,603,008 B1 * | 8/2003 | Ando et al. | 546/269.7 |
| 8,221,769 B2 | 7/2012 | Szalay et al. | |
| 2006/0035382 A1 | 2/2006 | Shinozaki et al. | |
| 2007/0082929 A1 * | 4/2007 | Gant et al. | 514/338 |
| 2008/0146605 A1 * | 6/2008 | Gant et al. | 514/299 |
| 2009/0075388 A1 | 3/2009 | Kainosho et al. | |
| 2010/0160248 A1 | 6/2010 | Shchepinov | |

FOREIGN PATENT DOCUMENTS

| | | |
|---|---|---|
| EP | 1548116 | 6/2005 |
| FR | 2721518 | 12/1995 |
| JP | 2001-514239 | 9/2001 |
| JP | 2001-519355 | 10/2001 |
| JP | 2002-513911 | 5/2002 |
| JP | 07-230879 | 9/2007 |
| JP | 2007-230876 | 9/2007 |
| JP | 2009-528260 | 8/2009 |
| JP | 2009-536925 | 10/2009 |
| WO | WO 2004-029254 | 4/2004 |
| WO | WO 2007/081910 | 7/2007 |
| WO | WO2007102030 | 9/2007 |
| WO | WO 2007/126457 | 11/2007 |
| WO | WO 2009/017833 | 2/2009 |
| WO | WO2009114809 | 9/2009 |

OTHER PUBLICATIONS

Ren et al. "Simultaneous metabolic labeling of cells with multiple amino acids: Localization and dynamics of histone acetylation and methylation" Proteomics Clin. Appl., 2007, vol. 1, pp. 130-142.*
Roomi et al. "In Vitro and In Vivo antitumorigenic Activity of a mixture of Lysine, Proline, Ascorbic Acid, and Green Tea Extract on Human Breast Cancer Lines MDA-MB-231 and MCF-7" Medical Oncology, 2005, vol. 22, No. 2, pp. 129-138.*
Wolen, R.L. "The Application of Stable Isotopes to Studies of Drug Bioavailability and Bioequivalence" J Clin Pharmacol, 1985, vol. 25, pp. 419-424.*
Haskins, N.J. "The Application of Stable Isotopes in Biomedical Research", Biomedical Mass Spectrometry, 1982, vol. 9, No. 7, pp. 269-277.*
Baillie, T.A. "The Use of Stable Isotopes in Pharmacological Research" Pharmacological Reviews, 1981, vol. 33, No. 2, pp. 81-132.*
Gouyette, A. "Synthesis of Deuterium-labelled Elliptinium and its Use in Metabolic Studies" Biomedical and Environmental Mass Spectrometry, 1988, vol. 15, pp. 243-247.*
Tonn et al. "Simultaeous Anaylysis of Diphenhydramine and a Stable Isotope Analog (2H10)Diphenhydramine Using Capillary Gas Chromatography with Mass Selective Detection in Biological Fluids from Chronically Instrumented Pregnant Ewes" Biological mass Spectrometry, 1993, vol. 22, pp. 633-642.*
Browne, T.R. "Stable Isotope Techniques in Early Drug Development: An Economic Evaluation" J Clin Pharmacol, 1998, vol. 38, pp. 213-220.*
Cannon, J.G., Chapter Nineteen in Burger's Medicinal Chemistry and Drug Discovery, Fifth Edition, vol. I: Principles and Practice, Wiley-Interscience 1995, pp. 783-802, 784.*
Asada et al; Stereochemistry of meso-α,ε Diaminopimelate Decarboxylase Reaction: The First Evidence for Pyriodoxal 5'-Phosphate Dependant Decarboxylation with Inversion of Configuration, Biochemistry, 1981, vol. 20, No. 24, pp. 6881-6886.
Bada et al; Isotopic Fractionation During Peptide Bond Hydrolysis, Geochimica et Cosmoschimica Acta, 1989, vol. 53, pp. 3337-3341.
Brandl et al; The biosynthesis of 3-(trans-2-Nitrocyclopropyl)alanine, a Constituent of the Signal Metabolite Hormaomycin; European Journal of Organic Chemistry, published online Dec. 20, 2004, vol. 2005, No. 1, pp. 123-135.
Cho et al; Cooperativity and anti-cooperativity between ligand binding and the dimerization of ristocetin A: asymmetry of a homodimer complex and implications for signal transduction; Chemistry & Biology; Mar. 1996; vol. 3, issue 3, pp. 207-215.

(Continued)

*Primary Examiner* — Kendra D Carter
(74) *Attorney, Agent, or Firm* — Knobbe, Martens, Olson & Bear, LLP

(57) ABSTRACT

Methods of treatment and substances for treatment of cancer may use or cause the creation of isotopically modified lysine at levels that do not occur naturally.

23 Claims, No Drawings

(56) References Cited

OTHER PUBLICATIONS

Dalle-Donne et al; Protein carbonylation in human diseases; Trends in Molecular Medicine; Apr. 2003, vol. 9, No. 4, pp. 169-176.
Demidov, V.; Heavy isotopes to avert ageing?; Trends in Biotechnology; Aug. 2007, vol. 25, No. 9, pp. 371-375.
Ikeya et al; Evaluation of stereo-array isotope labeling (SAIL) patterns for automated structural analysis of proteins with CYANA, Magnetic Resonance in Chemistry, Jul. 2006, vol. 44, spec. No. S152-S157.
International Search Report and Written Opinion dated Jun. 3, 2009 for PCT/US2009/037161.
International Search Report dated Jun. 12, 2007 for PCT/GB2007/050112.
Kelland et al; Stereochemistry of Lysine Formation by meso-Diaminopimelate Decarboxylase from Wheat Germ: Use of 1H-13C NMR Shift Correlation to Detect Stereospecific Deuterium Labeling, Biochemistry, Jun. 1985, vol. 24, No. 13, pp. 3263-2367.
Kushner et al; Pharmacological uses and perspectives of heavy water and deuterated compounds; Canadian Journal of Physiology and Pharmacology; Feb. 1999; vol. 77, pp. 79-88.
Lichtenstein et al; Comparison of deuterated leucine, valine and lysine in the measurement of human apolipoprotein A-I and B-100 kinetics; Journal of Lipid Research; 1990; vol. 31, No. 9, pp. 1693-1702.
Oba et al; A simple route to L-[5,5,6,6-D4] lysine starting from L-pyroglutamic acid, Japanese Journal of Deuterium Science, 2006, vol. 12, No. 1, pp. 1-5.
Raap et al; Enantioseletive syntheses of isotopically labeled a-amino acids. Preparation of (ε-13C)-L-α-aminoadipic acid and five isotopomers of L-lysine with 13C, 15N, and 2H in the δ- and ε-positions; Recueil de Travaux Chimiques de Pays-Bas, 1990, vol. 109, No. 4, pp. 277-286.
Ren et al; Simultaneous metabolic labeling of cells with multiple amino acids: localization and dynamics of histone acetylation and methylation, Proteomics: Clinical Applications; Jan. 2007; vol. 1, No. 1, pp. 130-142.
Scholl et al; Synthesis of 5,5,6,6-D4-L-lystine-aflatoxin B1 for use as a mass spectrometric internal standard; Journal of Labelled Compounds & Radiopharmaceuticals; Oct. 2004; vol. 47, No. 11, pp. 807-815.
Shchepinov, Mikhail; Reactive Oxygen Species, Isotope Effect, Essential Nutrients, and Enhanced Longevity; Rejuvenation Research; 2007; vol. 10, No. 1, pp. 47-59.
Tang et al; Kinetic and biochemical analysis of the mechanism of action of lysine 5, 6-aminomutase; Archives of Biochemistry and Biophysics; Oct. 2003; vol. 418, No. 1, pp. 49-54.
Wade, David; Deuterium isotope effects on noncovalent interactions between molecules; Chemico-Biological Interactions; 1999; vol. 117, No. 3, pp. 191-217.
Written Opinion dated Sep. 8, 2008 for PCT/GB2007/050112.
Finglas et al, Use of an oral/intravenous dual-label stable-isotope protocol to determine folic acid bioavailability fortified cereal grain foods in women, The Journal of Nutrition, vol. 132, No. 5, pp. 936-939, May 2002.
Geboes et al, Validation of a new test meal for a protein digestion breath test in humans, The Journal of Nutrition, vol. 134, No. 4, pp. 806-810, Apr. 2004.
Notice of Reasons for Rejection dated Aug. 24, 2011 for Japanese Patent Application No. 2008-557833.
Notice of Rejection dated Jul. 16, 2013 for Japanese Patent Application No. 2010-550906.
Pestov et al; Control of lysyl oxidase activity through site-specific deuteration of lysine; Bioorganic & Medicinal Chemistry Letters; vol. 21 (2011) pp. 255-258.
Netke et al; A Specific Combination of Asorbic Acid, Lysine, Proline and Epigallocatechin Gallate Inhibits Proliferation and Extracellular Matrix Invasion of Various Human Cancer Cell Lines; Emerging Drugs; vol. II (2003), PJD Publications Limited, Westbury NY (printed from Dr. Rath Health Foundation).
Rath and Pauling; Plasmin-Induced Proteolysis and the Role of Apoprotein(a), Lysine, and Synthetic Lysine Analogs; Journal of Orthomolecular Medicine; vol. 7, No. 1, (1992).
Shchepinov and Pestov; Isotope Effect, Essential Diet Components, and Prospects of Aging Retardation; Russian Journal of General Chemistry; vol. 80, No. 7 (2010) pp. 1514-1522.
Japanese Office Action for Japanese Patent Application No. 2010-550906 dated Feb. 10, 2014 by Japanese Patent Office.
N Nagan et al., "Modulation of lysyl oxidase activity toward peptidyl lysine by vincinal dicarboxylic amino acid residues", J.Biol. Chem., vol. 269, No. 35, 1994, pp. 22366-22371.
Extended European Search Report for European Patent Application No. 09721064.5 dated Dec. 17, 2014 by European Patent Office.

* cited by examiner

THERAPIES FOR CANCER USING ISOTOPICALLY SUBSTITUTED LYSINE

CROSS-REFERENCE TO RELATED APPLICATIONS

This application claims priority to U.S. provisional application No. 61/036,841 filed Mar. 14, 2008 which is incorporated herein by reference.

BACKGROUND

Lysyl oxidases (LOX, LOXL, LOXL2, etc.; amine oxidase family) are Cu-dependent enzymes that oxidize lysine into allysine (α-aminoadipic-δ-semialdehyde) [Kagan H M. et al., *J. Cell. Biochem.* 2003; 88:660]. LOX have been implicated in crosslink formation in stromal collagens and elastins. LOX are elevated in hypoxic tumors and affect cell motility, tumor development and progression of metastasis [Kirschmann D A. et al., *Cancer Res.* 2002; 62:4478]. This elevation is mechanistically important for breast cancer metastasis and invasion as well as in other cancers including colon and esophagus [Fong S F, et al. genes *Chromosomes Cancer* 2007; 6:644], and is based on the formation of Schiff-base linkages (aldehyde+amine) or aldol condensation products (aldehyde+aldehyde), allowing cancer cells to latch on to other cells/tissues. There are other mechanisms of LOX involvement into metastasis progression—for example, the recruitment of bone marrow—derived cells [Erler J T et al. Nature 2006; 440:1222-1226; Erler J T. et al., *Cancer Res.* 2006; 66:10238; Erler I T et al. Cancer Cell 2009; 15:35-44 ] for a so-called premetastatic niche formation.

LOX oxidises Lys of collagens, elastins and other proteins to allysine and/or

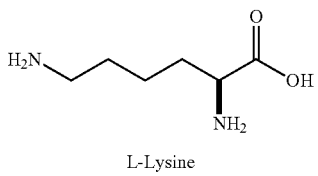

L-Lysine

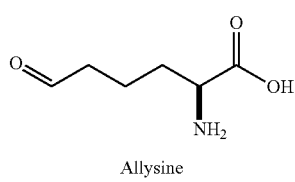

Allysine

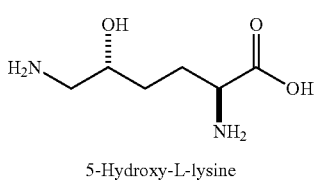

5-Hydroxy-L-lysine 5-hydroxylysine. These can then form cross-links, for example as shown below:

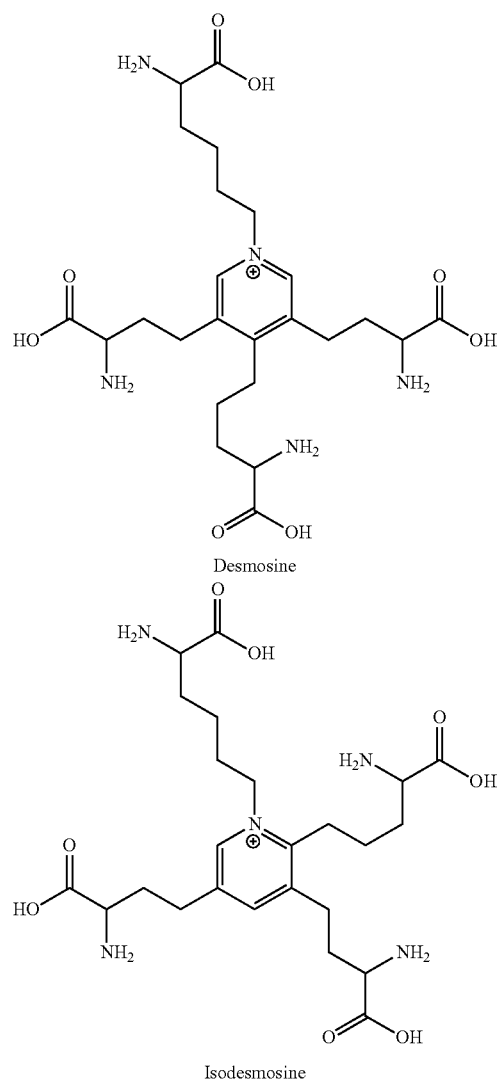

Desmosine

Isodesmosine

A reaction important in metastatic development. It is therefore desirable to reduce the activity of lysyl oxidase in cancer. As with any cancer treatment, it is also desirable that this does not completely block the enzyme activity, so as to minimize the adverse effects of therapy on other aspects of physiology.

It is therefore desirable to reduce the activity of extracellular LOX in cancer. Some current approaches involve LOX inhibitors (e.g. β-aminopropionitrile [Jackson L E. et al., *Biochem. Biophys. Res. Commun.* 1991; 179:939]), sequestration of Cu, and the use of antibodies [Erler J T et al., Nature 2006; 440:1222]. As with any cancer treatment, it is also desirable that this does not completely block the enzyme activity, so as to minimize the adverse effects of therapy on other aspects of physiology. For example, inhibition of LOX is known to cause increased elasticity of blood vessels etc., leading to aneurisms. Besides, these methods are likely to be immunogenic, as well as bringing further complications such as toxicity.

It is known that the rate of some reactions breaking or forming chemical bonds is affected by the nature of the isotopes of the atoms, which the bond links. In general, bonds terminating in a heavy isotope will be less liable to cleavage than a bond terminating in a lighter isotope. Of particular note is that bonds between hydrogen atoms and other atoms are less liable to breakage if the hydrogen is $^2H$ rather than $^1H$. A similar effect is seen when comparing the rate of cleavage of a bond between a carbon atom and another atom, where bonds with $^{13}C$ are less liable to cleavage than bonds with $^{12}C$. This is known as the Kinetic Isotope Effect, and is well described. Many isotopes are known to show this effect, as is described in *Isotope effects in chemical reactions*. (C. J. Collins, N. S. Bowman (eds.) 1970). It is known that these effects are also manifest in enzyme-catalyzed reactions, as described in. *Isotope effects on enzyme-catalyzed reactions* (Cleland, W. W., M. H. O'Leary, and D. B. Northrop (eds.) 1976).

SUMMARY

The KIE may be used to reduce the activity of lysyl oxidase without blocking its activity. Embodiments of this invention provide for 2,6-diamino-6,6-dideuterohexanoic acid; 2,6-diamino-5,5,6,6-tetradeuterohexanoic acid or their esters or amides, and for the use of such compounds in a treatment for a disease in which lysyl oxidase is important.

Embodiments of the invention also provide for administering supplementation by any compounds containing higher than naturally occurring prevalences of isotopes that yield stabilization of lysine via the kinetic isotope effect via incorporation of the higher than naturally occurring heavy isotope into the lysine-containing moieties in the body according to the Formulae I, II, and III described below for stabilized lysine.

DETAILED DESCRIPTION OF THE PREFERRED EMBODIMENT

In one aspect, a compound has the structure according to Formula (I)

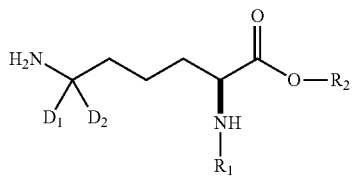

FORMULA (I)

wherein either $D_1$ or $D_2$ or both $D_1$ and $D_2$ are deuterium ($^2H$); wherein $R_1$ is H or a blocking group, wherein; $R_2$ is an amino acid or a peptide or a protein or part of a protein, or an aliphatic, aromatic, or substituted aliphatic or substituted aromatic acyl group.

The composition is not a naturally occurring composition such as lysine or lysine derivatives, which contain a mixture of components, which contain heavy and light isotopes. The amount of heavy isotopes in the composition will be greater than the natural occurrence, such as an enrichment that is greater than 20% more than the naturally occurring heavy isotope. The heavy isotope enrichment may be an enrichment at a single position or several positions.

It will be understood by one skilled in the art that the term "blocking group" is any group which can be linked to an amino or a carboxylate function and which is likely to be cleaved enzymatically or chemically in vivo to yield the free amine or carboxylic acid respectively, or which can be displaced in vivo to make a naturally occurring metabolite of the amino acid. Such groups could comprise an amino acid, a peptide, a protein or part of a protein, an ester (e.g., linking $R_2$ to an alcohol or phenol), an amide (e.g., linking $R_2$ to an amine or $R_1$ to a carboxylate group), or other more complex groups such as BOC, Fmoc or other well-known groups.

It will be appreciated by one skilled in the art that the term Deuterium in some embodiments refers to cases where the majority of molecules in a preparation have $^2H$ in the relevant position in the molecule, but that there will be in the preparation a minority of molecules where there is a $^1H$ in that position.

In a further embodiment, the invention also provides for the compounds of Formulae II and III, which have other carbon atoms protected with deuterium. It may also be

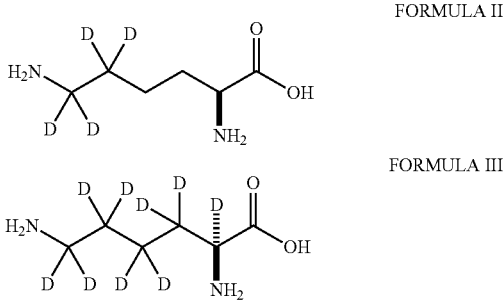

desirable to use carbon-13 instead of carbon-12, for example, at position 6, or for 1, 2, 3, 4, 5, or 6 carbon atoms of Lys, to further increase the KIE.

In further embodiments, the compound or a mixture of compounds of Formula (I-III) may be used in a foodstuff, and are useful for the delay of the development of cancer, or any other disease associated with enhanced activity of lysine degrading enzymes or degraded forms of lysine itself.

In a further embodiment, the use of a compound or a mixture of compounds of Formula (I) may be used in a nutritional supplement for the treatment of a disease. Such supplement may consist substantially of compounds according to Formula (I) or may have such compounds as a minor component, providing that compounds of Formula (I) provide the majority of the lysine in the supplement by mass.

In a further embodiment, this invention provides for a medicament including a compound of Formula (I) useful for the treatment of a disease. The medicament may consist of a compound or a mixture of compounds according to Formula (I) in a pharmaceutically acceptable salt. The medicament may also include bulking agents or fillers, excipients, agents to assist or retard solution of the compounds according to Formula (I), agents to modify or mask taste, agents to assist in the manufacture of tablets or capsules, agents to protect the compounds during gastrointestinal transit and other materials well-known to those ordinarily skilled in the art of drug formulation. The medicament may be in the form of a powder, a table, a capsule, a liquid suitable for injection or injection, a spray, a cream, an ointment, an aerosol, a suppository or other forms well known to those skilled in the art.

In a further embodiment, this invention includes methods of administering or dosing non-naturally occurring levels of heavy isotope to subjects such that the stabilized compositions of Formula I, II, or III result. Subjects may include mammals such as humans, livestock, and laboratory animals, such as mice, rats, rabbits, monkeys or other lower order animals.

Combination therapies with e.g. known anti-cancer or anti-fibrotic treatment are also contemplated.

In some embodiments, a subject may be administered, for example, about 10%, 20%, 50%, 200% or 1000% of the average dietary content of lysine, so as to either compete with dietary lysine of the naturally occurring composition or overwhelm it. Normal dietary levels are approximately 2-3 grams per day, and of course vary with diet. For example, a subject may be administered a catalytic amount of about 0.2, 0.3, 0.4, 0.5, 0.6, 0.7, 0.8. or 0.9 grams of lysine or lysine derivative per day described herein with greater than the natural occurrence of heavy isotope; a competitive amount of about 1, 2, 3, or 4 grams of lysine or lysine derivative per day described herein with greater than the natural occurrence of heavy isotope; or an overwhelming amount of about 4, 5, 6, 7, 8, 9, 10, 11, 12, 13, 14, 15, 16, 17, 18, 19, 20, 30, 40, 50, 60, 70, 80, 90, or 100 g of lysine or lysine derivative described per day herein with greater than the natural occurrence of heavy isotope.

A further aspect of the invention provides a pharmaceutical composition of the compound or composition described herein.

A pharmaceutical composition containing the active ingredient may be in a form suitable for oral use, for example, as tablets, troches, lozenges, aqueous or oily suspensions, oil-in-water emulsions, dispersible powders or granules, emulsions, hard or soft capsules, or syrups or elixirs. Such compositions may contain excipients such as bulking agents, solubilisation agents, taste masking agents, stabilisers, colouring agents, preservatives and other agents known to those ordinarily skilled in the art of pharmaceutical formulation.

A pharmaceutical composition containing the active ingredient may also be administered in the form of suppositories for rectal administration of the drug. These compositions can be prepared by mixing the drug with a suitable non-irritating excipient, which is solid at ordinary temperatures but liquid at the rectal temperature and will therefore melt in the rectum to release the drug. Such materials are cocoa butter and polyethylene glycols.

A pharmaceutical composition may also be suitable for delivery by inhalation to the nose, throat or lungs. Such compositions may be prepared by pre-forming compounds of the invention into particles suitable for inhalation together with other materials, or dissolving compounds of the invention in a material suitable for forming an aerosol.

A pharmaceutical composition may also be suitable for delivery by topical application, as a spray, cream, ointment, lotion, or as a component or additive to a patch, bandage or wound dressing. In addition the compound can be delivered to the site of the disease by mechanical means, or targeted to the site of the disease through the use of systemic targeting technologies such as liposomes (with or without chemical modification that provides them with affinity for the diseased tissue), antibodies, aptamers, lectins, or chemical ligands with affinity for aspects of the diseased tissue that are less abundant or not present on normal tissue.

A pharmaceutical composition of the invention may also be in a form suitable for administration by injection. Such compositions may be in the form of a solution, a suspension or an emulsion. Such compositions may include stabilizing agents, antimicrobial agents or other materials to improve the function of the medicament. This invention also encompasses dry, desiccated or freeze-dried forms of compounds of the invention, which can readily be formed or reconstituted into a solution suspension or emulsion suitable for administration by injection, or for oral or topical use.

EXAMPLES

Deuterated Lysine was synthesised from L-Lys as shown below:

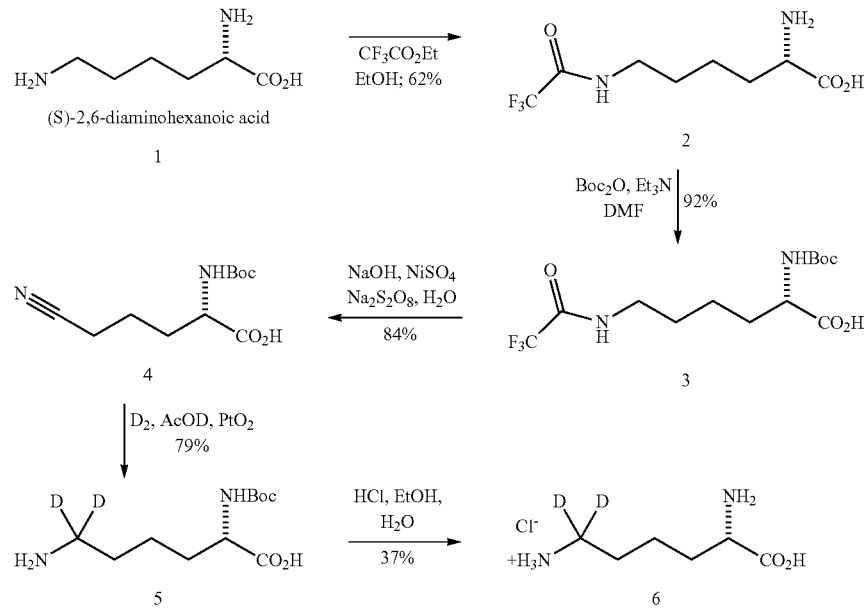

Example 1

(S)-6-trifluoroacetylamino-2-aminohexanoic acid (2)

Sodium (4.6 g; 0.2 mol) was dissolved in 200 ml of ethanol (abs). To this solution, 18.25 g (0.1 mol) of lysine (Sigma-Aldrich) hydrochloride (1) was slowly added with stirring. The mixture was stirred for 1 hour, and the precipitate filtered away. To the remaining solution cooled on ice, 21.3 g (0.15 mol) of ethyltrifluoroacetate was slowly added with intense stirring. The solution was brought up to rt and stirred for another 2 hours. 6 g (0.1 mol) of AcOH was added, and the precipitate formed was washed with EtOH and acetone. Yield: 15 g (62%). MALDI-TOF, positive mode: 242.455 (MI+1; 67%).

Example 2

(S)-6-trifluoroacetylamino-2-(tert-butoxycarbonylamino)-hexanoic acid (3)

To compound (2) (3.63 g; 0.015 mol) suspended in 40 ml DMFA, 3.03 g (0.03 mol) of TEA and 3.6 g (0.0165 mol) of di-tert-butylcarbonate were added, and the reaction mixture was stirred for 3 hours at rt. The mixture was then diluted 3-fold by water and acidified by HCl to pH 2. The product was extracted with EtOAc (100 ml), washed with water, brine and dried ($MgSO_4$). The solvent was removed in vacuo to yield 4.7 g (92%) of the title compound. The analytical data for (3) was identical to that reported in literature.

Example 3

(S)-2-(tert-butoxycarbonylamino)-5-cyanopentanoic acid (4)

To a solution of 0.56 g (0.014 mol) of NaOH in 40 ml of water, 2.39 g (0.007 mol) of compound (3), 0.2 g of $NiSO_4 \times 7H_2O$, and 3.33 g (0.014 mol) of sodium persulfate was added. Over the next 3 hours, 1.12 g (0.028 mol) of NaOH was added to this solution in small portions with stirring. The resulting mixture was stirred overnight. The excess of oxidiser was neutralised with sodium sulphite. The mixture was acidified by HCl to pH 2. The product was extracted with EtOAc (100 ml), washed with water, brine and dried ($MgSO_4$). The compound was purified by CC on silica gel (eluent: chloroform). Yield: 1.42 g (84%). MALDI-TOF, positive mode: 262.978 (MI+Na; 43%).

Example 4

(S)-6-amino-6,6-dideutero-2-(tert-butoxycarbonylamino)-hexanoic acid (5)

Method 1. To a solution of 100 mg (0.41 mmol) of nitrile (4) in 2 ml of AcOD (98% isotopic purity), 15 mg (15 mass-%) of $PtO_2$ was added. The mixture was stirred in the atmosphere of $D_2$ (98% isotope purity) at rt for 3 hours, filtered, and evaporated at reduced pressure. The residue was purified (CC, silica; eluent: chloroform-MeOH-AcOH). Yield: 65 mg (63%) as oil. Isotope purity was determined to be about 90% judging by the NMR signal ratio (2.7 md and 3.6 md; the ratio is 2:1 for Lys, but $D_2$-Lys should not have a signal at 2.7 md).

Method 2. To a solution of nitrile (4) (1.5 g, 6.2 mmol) in 30 ml of AcOD (97% isotopic purity), 242 mg (15 mass-%) of $PtO_2$ was added. Reaction mixture was stirred in the atmosphere of $D_2$ (97% isotope purity) at rt for 20 hours, filtered, and evaporated at reduced pressure. The residue was purified (CC, silica; eluent: chloroform-MeOH-AcOH). Yield: 1.2 g (79%) as oil. Isotope purity was determined to be >85% judging by the NMR signal ratio (See Method 1).

Example 5

(S)-2,6-diamino-6,6-dideuterohexanoic acid (6)

To a solution of 1.2 g (4.88 mol) of deuterated Boc-Lys (5) in EtOH (5 ml), concentrated HCl (2 ml) was added. The reaction mixture was warmed up to 50° C., stirred for 30 min., and the solvent was removed in vacuo. The residue was dissolved in 20 ml EtOH, brought to a boil, and 0.5 g (6.3 mmol) of Py was added dropwise. The mixture was cooled down and left at +4° C. overnight. Yield: 0.33 g (37%; after drying) of product as white crystals. MALDI-TOF, positive mode: 149.286 (MI+H; 73%).

Example 6

Expression, Purification and Folding of Recombinant LOX

Mouse LOX cDNA corresponding to the processed enzyme (amino acid coordinates 163-411) was amplified by RT-PCR using mouse heart total RNA and a proofreading DNA polymerase. The PCR product was cloned into pQE30 expression (Qiagen, Valencia, Calif.) vector at BamH I site. The expression was induced by addition to the log-phase *E. coli* cells of 1 mM IPTG and incubation for 4 h at 37° C. The cells were lysed in a 6M urea buffer, cleared by centrifugation and incubated with NTA-$Ni^{2+}$-Agarose (Qiagen, Valencia, Calif.). The agarose was thoroughly washed with 6M urea and the bound protein eluted with imidazole in 6M urea. For refolding, the dialysis protocol described by [Jung S T et al., Protein Exper Purif. 2003; 31:240-246] was used, but the starting concentration of N-lauroylsarcosine was increased and an additional dialysis step against glutathione was included to assist correct folding.

Example 7

Functional Non-Radioactive Assay of LOX Enzymatic Activity

A non-radioactive cross-linking assay was developed that allows detection of oxidized lysine residues on solid support using reaction with a biotinylation reagent and an enzyme assay. Collagen from cold-water fish was immobilized on EIA plates (Costar), briefly incubated with hydroxylamine, thoroughly washed and incubated with the recombinant LOX in a phosphate buffer with free access to air as a source of oxygen. This was followed by washing, reaction with biotin hydrazide, ExtrAvidin-peroxidase and development with orthophenylenediamine. γ-aminopropionitrile was used as an inhibitor of LOX whenever necessary.

What is claimed is:

1. A method, comprising:
    selecting a human patient in need of treatment for a condition associated with degradation of lysine-containing moieties, wherein the condition is breast cancer or fibrosis;
    repeatedly delivering to the patient an effective lysine-oxidation-inhibiting material consisting essentially of a compound of Formula (I), Formula (II), or Formula (III);

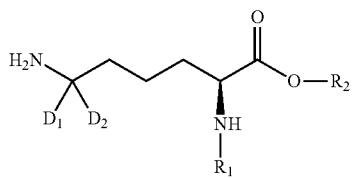

FORMULA (I)

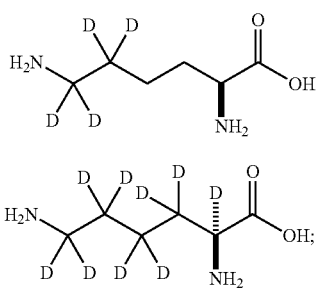

FORMULA II

FORMULA III wherein D is deuterium;
wherein a carbon in Formula (I), (II), or (III) is optionally carbon-13; and
wherein the carbon-13, deuterium or both are enriched at least 20% more individually or collectively in comparison to naturally occurring carbon-13, deuterium or both at the same positions in the compound; and
thereby treating the condition by affecting an alteration of the isotopic composition of lysine-containing moieties in the body of the patient to effectively reduce the extent of degradation of lysine-containing moieties in vivo in the patient.

2. The method of claim 1, wherein the method reduces oxidation of the delivered compound of formula I, II, or III, or the lysine-containing moieties, by a lysyl oxidase.

3. The method of claim 1, wherein the lysine-oxidation-inhibiting material is administered to the patient as a foodstuff or supplement.

4. The method of claim 2, wherein the lysine-oxidation-inhibiting material reduces tumor growth in the patient.

5. The method of claim 2, wherein the lysine-oxidation-inhibiting material reduces angiogenesis in the patient.

6. The method of claim 2, wherein reducing degradation of lysine containing moieties via non-naturally occurring levels of heavy isotope reduces fibrosis in the patient.

7. The method of claim 4, wherein said tumor is a primary tumor or a metastatic tumor.

8. The method of claim 7, wherein metastatic tumor burden of the patient is stabilized.

9. The method of claim 1, wherein the fibrosis is a liver fibrosis, a lung fibrosis, a kidney fibrosis, a cardiac fibrosis or schleroderma.

10. The method of claim 9, wherein said kidney fibrosis is diabetic nephropathy, glomerulosclerosis, diabetic nephropathy, vesicoureteral reflux, tubulointerstitial renal fibrosis or glomerulonephritis.

11. The method of claim 1, wherein the lysine-oxidation-inhibiting material is the compound of formula (I).

12. The method of claim 11, wherein the lysine-oxidation-inhibiting material is the compound of formula (I) wherein both $D_1$ and $D_2$ are deuterium ($^2H$).

13. The method of claim 1, wherein the lysine-oxidation-inhibiting material is the compound of formula (II).

14. The method of claim 1, wherein the lysine-oxidation-inhibiting material is the compound of formula (III).

15. The method of claim 1, wherein the activity of a LOX enzyme is reduced.

16. The method of claim 15, wherein the activity of the LOX enzyme is not completely blocked.

17. The method of claim 1, wherein the lysine-oxidation-inhibiting material is administered to the patient as part of the patient's diet.

18. The method of claim 17, wherein the oxidation of collagen or an elastin is reduced.

19. The method of claim 1, wherein the lysine-oxidation-inhibiting material is incorporated into the patient's body.

20. The method of claim 1, wherein at least one carbon in the lysine-oxidation-inhibiting material is carbon-13.

21. The method of claim 1, wherein the lysine-oxidation-inhibiting material is stabilized against a chemical oxidation of a lysyl oxidase.

22. The method of claim 1, wherein the lysine-oxidation-inhibiting material is stabilized against an enzymatic oxidation of a lysyl oxidase.

23. The method of claim 1, wherein the lysine-oxidation-inhibiting material is administered to the patient orally, intravenously, or topically.

* * * * *